(12) United States Patent
Wolf et al.

(10) Patent No.: US 7,721,605 B2
(45) Date of Patent: May 25, 2010

(54) MECHANICAL OSCILLATOR ACTIVATED OR DEACTIVATED BY A PREDETERMINED CONDITION

(75) Inventors: Henry Alan Wolf, Morristown, NJ (US); Manuel S. Alvarez, Warrenton, VA (US); James E. Feather, Burke, VA (US); George P. Akehurst, Belvidere, NJ (US)

(73) Assignee: Exxonmobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 12/156,576

(22) Filed: Jun. 3, 2008

(65) Prior Publication Data

US 2008/0314150 A1 Dec. 25, 2008

Related U.S. Application Data

(60) Provisional application No. 60/934,711, filed on Jun. 15, 2007.

(51) Int. Cl.
*G01H 13/00* (2006.01)
*G01L 11/00* (2006.01)

(52) U.S. Cl. .............................. 73/579; 73/651; 73/702; 73/709

(58) Field of Classification Search .................. 73/579, 73/580, 590, 651, 702, 709
See application file for complete search history.

(56) References Cited

U.S. PATENT DOCUMENTS

| | | | | |
|---|---|---|---|---|
| 3,310,983 A * | 3/1967 | Boulais et al. | .......... | 246/169 A |
| 3,630,216 A | 12/1971 | Kelly | | |
| 4,906,053 A | 3/1990 | Kawai | | |
| 5,036,705 A * | 8/1991 | Gaines | .................... | 73/514.14 |
| 5,559,358 A * | 9/1996 | Burns et al. | ................. | 257/431 |
| 5,734,098 A * | 3/1998 | Kraus et al. | ................ | 73/61.62 |
| 6,311,557 B1 * | 11/2001 | Davis et al. | ............. | 73/514.31 |
| 6,374,677 B1 * | 4/2002 | Berlin et al. | .................. | 73/662 |
| 6,422,083 B1 * | 7/2002 | Hobbs | ........................ | 73/663 |
| 7,148,611 B1 * | 12/2006 | Liu | ............................ | 310/366 |
| 7,514,853 B1 * | 4/2009 | Howe et al. | ................. | 310/346 |
| 2002/0178787 A1* | 12/2002 | Matsiev et al. | ............ | 73/24.01 |
| 2005/0145019 A1 | 7/2005 | Matsiev et al. | | |

\* cited by examiner

*Primary Examiner*—Hezron Williams
*Assistant Examiner*—Rose M Miller (57) ABSTRACT

The present invention is a mechanical oscillator for detection and measurement of corrosive foreign materials. The elements include a mechanical oscillator that is mechanically excited, wherein the mechanical oscillator has a resonant frequency, f, and a quality factor, Q. A fuse fixed to the oscillator to change oscillator amplitude to and from essentially zero to resonance amplitude. In a preferred embodiment, the mechanical oscillator has the shape of a tuning fork where one region is compatible with the service fluid and the other region is incompatible with the service fluid or other contaminant. The sensor alarms when a measured amount of the incompatible material has been removed or the physical strength of the material has been compromised.

16 Claims, 6 Drawing Sheets

Swelling Material Activates in the Presence of Select Materials and Prevents Tine motion and Oscillation Support structure for fusing element 90

Fusing element frabricated from material that swells 80

FIG. 1

Metal Fusing Element Rigidly Binds the Tines Attached via Weldment

FIG. 2a

Metal Element Rigidly Binds the Tines Attached via Epoxy Fuse

FIG. 2b

Example Using a Metallic Element for the Rigid Fuse of Figure 2a

FIG. 3a

Example Using a Rigid Connector Attached to the Tines Using Epoxy Fuse of Figure 2b

Example of a Pressure Fuse: Pressure Pushed the Damping Material to the Tines Stopping the Tine Motion Bellows structure 110

Fusing element fabricated from damping material 100

FIG. 5

Example Where Coating on Fork Tip Changes Resonance Enabling or Disabling Vibration Motion Coating material that dissolves 120

FIG. 6

MECHANICAL OSCILLATOR ACTIVATED OR DEACTIVATED BY A PREDETERMINED CONDITION

CROSS REFERENCE TO RELATED APPLICATION

This application claims the benefit of U.S. Provisional Application 60/934,711 filed Jun. 15, 2007.

BACKGROUND OF THE INVENTION

The present invention relates to the detection and measurement of corrosive or foreign materials. The invention may be applied generally to the detection of metal-loss by corrosion and/or erosion species in single or multiphase fluids. In particular, the present invention relates to the on-stream detection of metal-loss corrosion and/or erosion during an industrial production process. In other embodiments, the invention may be used to detect unwanted contaminants in an industrial process stream. The actual service environment may be aqueous, hydrocarbon, chemical, or a combination thereof.

Corrosive species involved in the production and processing of crude oil and hydrocarbons may cause metal-loss corrosion of production, transfer, storage, and processing equipment. Other types of corrosion degradation may also occur which do not result in metal loss but which nonetheless affect the integrity of the material of construction. Erosive species typically involve fluid and/or solids turbulence causing metal loss from mechanical actions rather than chemical. For example, these corrosive/erosive species may be hydrocarbon, hydrocarbon containing materials, or aqueous, or combinations thereof. Moreover, streams may be single or multiphase (solids, liquids, gases). The device of the instant invention can be used to generate an alarm based on remaining metal thickness or mechanical integrity of pressure a boundary thereby enabling maintenance scheduling.

A high performance, relatively low-cost detection of a predetermined amount of material loss or material degradation, as in the instant invention, would enable, for example, optimization utilization of corrosive crudes and corrosion inhibitor additions, and reductions in unplanned capacity loss, turnaround time, and inspection costs due to corrosion-induced equipment failures. For example, the instant invention would provide a direct, low-cost alarm when the corrosion allowance of the process containment has been expended. Additional value is achievable with the instant invention by the detection of tramp materials in a process stream which may be corrosive or problematic for the industrial production process. Further value is achievable with the application to monitoring metal-loss corrosion in equipment used for the extraction of crude oil from subsurface and sub sea deposits. Other operating modes are described where the instant invention can be configured as a pressure or temperature alarm. In these and other services, a by-product of the corrosion is scale or other depositions that are adherent to the containment surface. A feature of the instant invention is that the metal loss measurement is not compromised by these non-metallic depositions.

Current corrosion sensing technologies, for example electrical resistance probes, fall far short of the performance level required to achieve the economic incentives described above. Their shortcoming is that the probes' inherent signal variability caused by thermal changes, conductive deposits, and other factors that affect electrical resistance make them intrinsically unsuitable to provide a quantitative indication of material lost from corrosion/erosion. While conventional electrical resistance probes are based on understood theoretical principles, these probes often provide low reliability and poor sensitivity to corrosion rates due to limitations in their design and manufacture. The typical output is often difficult for estimating a quantitative corrosion rate. Another technology that may be used for this application for the material loss application is known as the corrosion the coupon. In this case, a coupon fabricated from the material of interest is inserted into the process stream. At a predetermined time, it is removed and examined and/or weighed to assess the amount of material that has been lost. A significant drawback of this approach is the safety implication of inserting or removing a coupon from an operating high temperature and/or high pressure industrial process. Another drawback of the current technology is the time lag necessary to adequately detect and verify a change in corrosion rates which can then subject the equipment being monitored to an unnecessarily extended period of high corrosion rates before corrective measures can be implemented.

U.S. Pat. No. 6,928,877 and US application 2006/0037399 both employ resonators and teach a relationship between the resonance frequency and mass change. The relationship taught by the prior art applies the well-known formulae relating oscillator mass to it resonance parameters. In particular, the prior art monitors frequency and Q. A deficiency in the prior art is that a quantitative relationship is not established between the material loss, corrosion product deposition and the resonance parameters of amplitude, frequency, and Q. The instant invention teaches away from the prior art by employing a binary monitoring of the oscillator amplitude or frequency. Continuous trending is not required. Clearly this finding is not obvious in light of the teachings of the prior art. In one embodiment, the instant invention has utilized that the oscillator can be immobilized by a fusing link.

The focus of U.S. Pat. Nos. 6,928,877 and 2006/0037399 is to provide a quantitative estimate of mass loss or deposition. Essentially, both provide an alarming function. The instant invention also provides an alarming function. Unlike the prior art where it is difficult to calibrate and predetermine the range for the alarm trigger, the instant invention has no such ambiguity. Once the fusing element is removed or broken, the instant invention goes into alarm mode. It is not necessary to estimate a range over which this alarm mode may initiate because the precise dimensions of the fused-element are known at the time of fabrication. In 2006/0037399 one approach to alarming is achieved by fabricating a hollow resonator. Then depending on the service, the alarming is achieved by filling or emptying the hollow space when the shell of the resonator holes through. Not only is this fabrication more complicated than the instant invention, but it does not provide a procedure to precisely predetermine the change in resonance parameters or to provide an exact measure of the material loss to achieve the alarm threshold. For the instant invention, the change in resonance parameters coincident with the detection threshold are abrupt.

SUMMARY OF THE INVENTION

The present invention is a sensor (described below) to detect a specified condition in a medium. This includes the detection and measurement of corrosive or foreign materials. The invention may be applied generally to the detection of metal-loss by corrosion and/or erosion species in single or multiphase fluids. In particular, the present invention relates to the on-stream detection of a pre-determined amount of metal-loss corrosion and/or erosion or a contaminant during an industrial production process. Application examples are readily found in refinery environments which are intended to operate without interruption for several years. Although on-stream inspection methods are available to provide information on the integrity of the pressure boundary, typically the most reliable inspection methods are scheduled on a periodic basis. The instant invention provides an on-stream continuous monitoring method to assess if a pre-established condition has been reached. This pre-established condition might necessitate a full on-stream inspection, process changes, a process shutdown to perform maintenance, etc. In some embodiments, the invention may be used to detect a pre-determined amount of material loss and in other embodiments the invention can detect unwanted contaminants in an industrial process stream. The actual service environment may be aqueous, hydrocarbon, chemical, or a combination. In another embodiment, the invention may be used to detect damage that affects the integrity of a material due to a reaction with the environment, such as a change in mechanical or physical properties, without significant material loss.

The sensor includes a mechanical oscillator. In the most general embodiment, the oscillator has a vibrating element such as tuning fork tines or rods. As examples, the cross-sectional shape of the tines or rods may be circular, or rectangular. These vibrating elements are attached to a diaphragm. There is also a fusing restricting tine motion that may react with the service fluid. The vibrating tine element includes a base and a tip region. Typically, the motion of the oscillator will be a maximum at the tip which will be the region associated with the maximum change to resonance parameters. The oscillator has a resonance frequency, f, and the quality factor associated with the resonance, Q. The resonance factor Q is inversely proportional to the total system damping. The mechanical excitation may be provided by the flow of the service fluid or by active excitation at the diaphragm. As an example, this active excitation may be provided by a piezoceramic, inductive, or magnetostrictive driver. When driven by an external energy source, such as a piezoceramic driver, it is not required to continuously provide the excitation. The excitation can be applied at the times it is desired to interrogate the corrosion sensor.

There are several embodiments to the present invention. In some embodiments, the oscillator changes from vibrating at or near resonance frequency to essentially vibrating with zero amplitude. In other embodiments, this change may be from zero amplitude to resonance amplitude. This change in the oscillation is caused by a reaction of a fusing element of the instant invention with its environment. Depending on the particular application, the fusing element may be metallic or non-metallic. In all cases, the amplitude of oscillation changes dramatically from essentially zero to resonance or resonance to essentially zero. An advantage of all these embodiments is that the alarm condition can be set without external corrections to account for changes in the oscillator resonance parameters caused by temperature, viscosity, density.

BRIEF DESCRIPTION OF THE DRAWINGS

FIG. 3a shows the result using a metallic element for the rigid fuse of FIG. 2a.

DETAILED DESCRIPTION OF THE PREFERRED EMBODIMENTS

Figure 1:
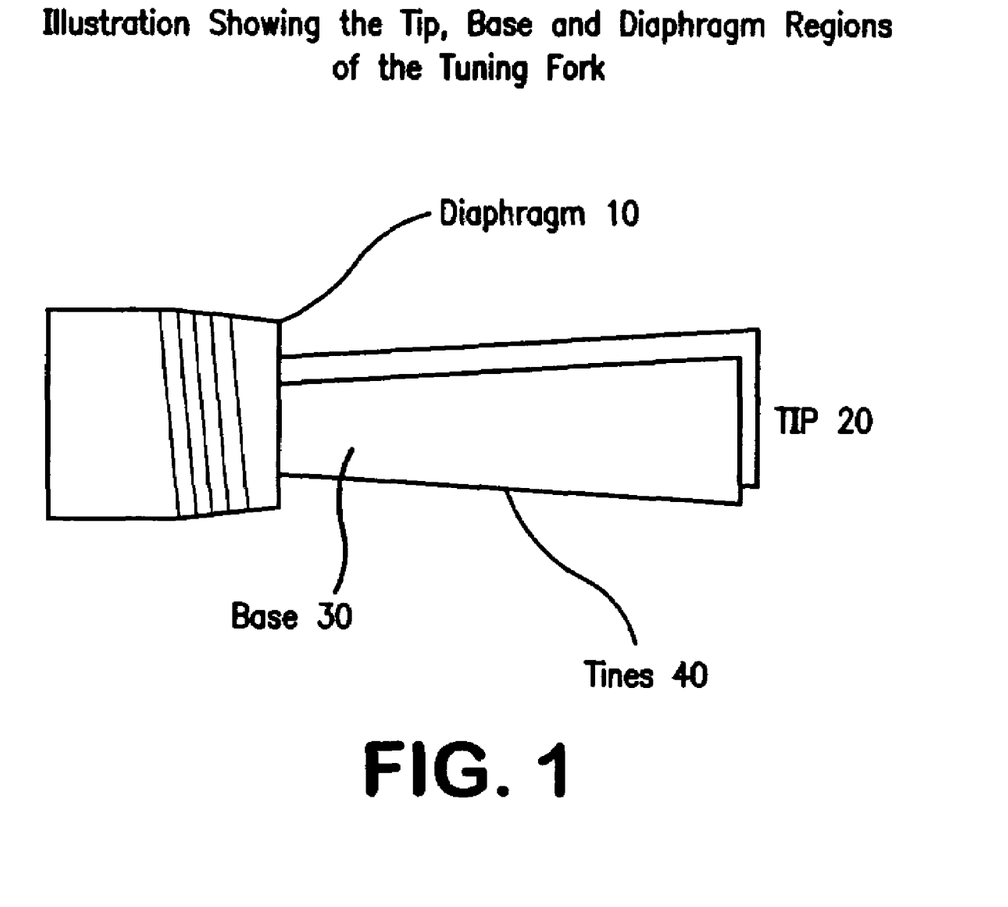
FIG. 1 shows a schematic drawing of a tuning fork oscillator indicating the tip, base, and diaphragm regions.

This invention is directed to commercial tuning fork technology. As shown in FIG. 1, the tuning fork consists of a two tines [40] attached to a diaphragm [10]. The tines are comprised of a tip [20] and a base [30] region. Various shapes are possible for the tines including round, hemi-cylindrical, and a non-uniform shape for the tip and base region. The existing commercial applications include the on-line in-situ measurement of fluid level, density and/or viscosity of process streams in a wide range of industries. The instant invention involves the measurement of changes in the resonant parameters (in particular amplitude) of a tuning fork immersed in a process stream to detect material loss. The current commercially available devices use the resonance parameters of frequency, Q, and amplitude to determine the density and the viscosity of the medium. The underlying assumption in these devices for measuring fluid level, density and/or viscosity is that the mass of the oscillator is fixed and its mechanical properties are fixed at the operating temperature. Another assumption is that there is no mass deposition on the tuning fork by the service fluid. Some commercial systems available include a temperature measurement to compensate for changes in mechanical properties. Moreover, in these commercial systems, the material used for the oscillator is compatible (e.g. non-corrosive) with the process fluid in the intended application.

The present invention uses the changes in the tuning fork resonance parameters caused by a corrosion/erosion mass loss. In the prior art, gradual changes of resonance parameters to measure material loss and/or the material loss rate are considered. In contrast, the instant invention alarms when a predetermined measure of material is lost. Although cited prior art also claims to alarm at certain levels of material loss, the accuracy of the alarming parameter is compromised by changes to the resonance conditions caused by variations in temperature, viscosity, and density of the service fluid. In cases where both deposition and corrosion are occurring simultaneously, there is a further complication of interpreting changes to the resonance parameters. The advantage of the instant invention is that the alarming is coincident with a precise measure of material loss independent of these parameters. In the case of the instant invention, the resonance device is fused to alarm when the fuse material is consumed. Since the fuse material is deposited prior to installing the device in the service fluid, a precise measure of the alarming condition can be pre-determined.

In the present invention, the resonance parameters are caused to make a definitive transition when a predetermined amount of material, the consumable fusing element, has been removed from the tuning fork resonator. This definitive transition involves a change from no or low tine motion to the tine motion associated with resonance. Or conversely, the transition may be from tine motion associated with resonance to the low level motion associated by moving off resonance. Various embodiments are enabled by the configuration of the consumable fusing element. The material of the fusing element is fabricated from materials that are not compatible (will corrode, erode or otherwise react) with the service fluid. The tines and the diaphragm shown in FIG. 1 are fabricated from materials that are compatible with the service fluid. Typically, only the fusing element is not compatible with the service fluid.

Embodiment where the Fusing Element is Rigid

Figure 2A:
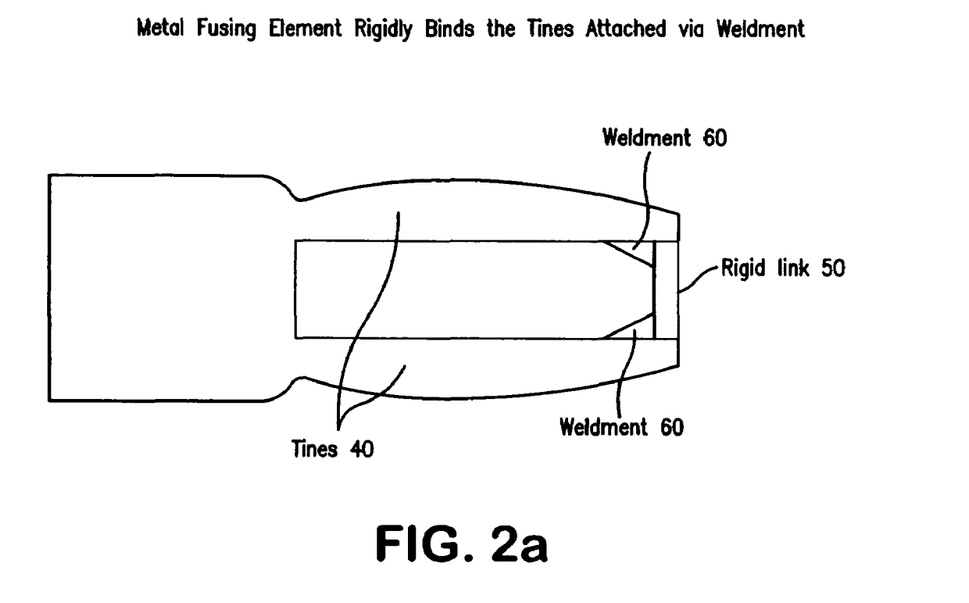
FIG. 2a illustrates an embodiment applying a fusing element that is rigidly and directly attached to both tines of a tuning fork via weldment.
Figure 2B:
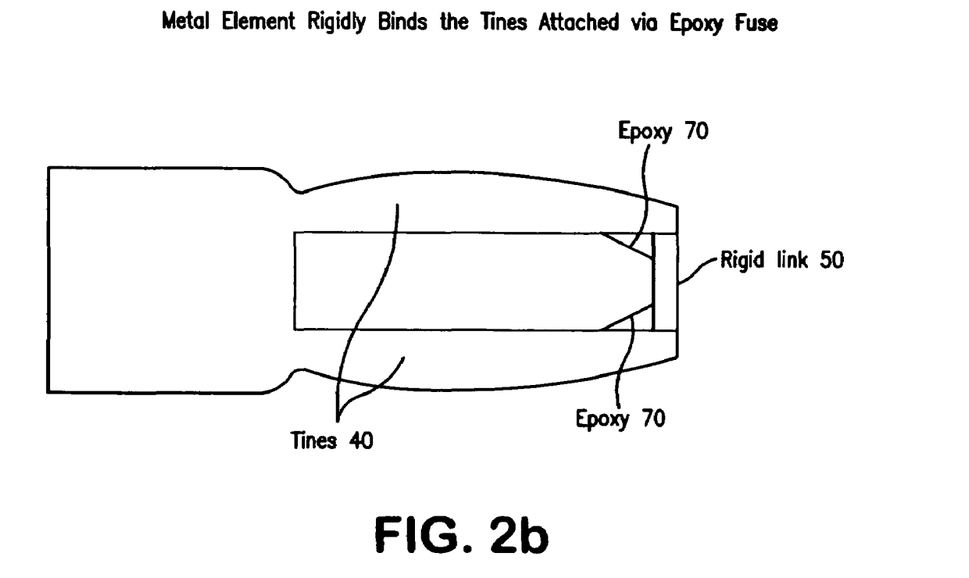
FIG. 2b illustrates an embodiment applying a rigid element immobilizing the tines that is attached to both tines of a tuning fork via an epoxy fusing element.

In this embodiment, the fuse element is comprised of a substantially rigid element [50]. In this embodiment, a link rigidly connects the tips of the two tines [40] (FIG. 2a and FIG. 2b). In FIG. 2a, the link is consumable and is welded to the tines. In FIG. 2b, the link is not consumable. The FIG. 2b link is attached to the tines by epoxy, the consumable (fusing) material. This rigid link in both cases prevents oscillation of the tines. The fuse material (metallic or nonmetallic) and dimensions are determined by the detection application. In FIG. 2a, the fuse (the consumable material) is the link itself. In FIG. 2b, the fuse is actually the epoxy [70]. For a corrosion/erosion application, typically the fuse material would be the same material as the material of interest. In some case this may be the pressure boundary material. In other cases it could be the material of internal components. The material dimensions would be selected based on the amount of material loss that would be of interest (e.g. the alarm point). When corrosion/erosion causes the fuse to break, the oscillator amplitude will experience a significant increase from a zero or very low value. Monitoring the resonance parameters (such as amplitude or Q) would trigger the alarm that the pre-established condition has been reached.

Figure 3A:
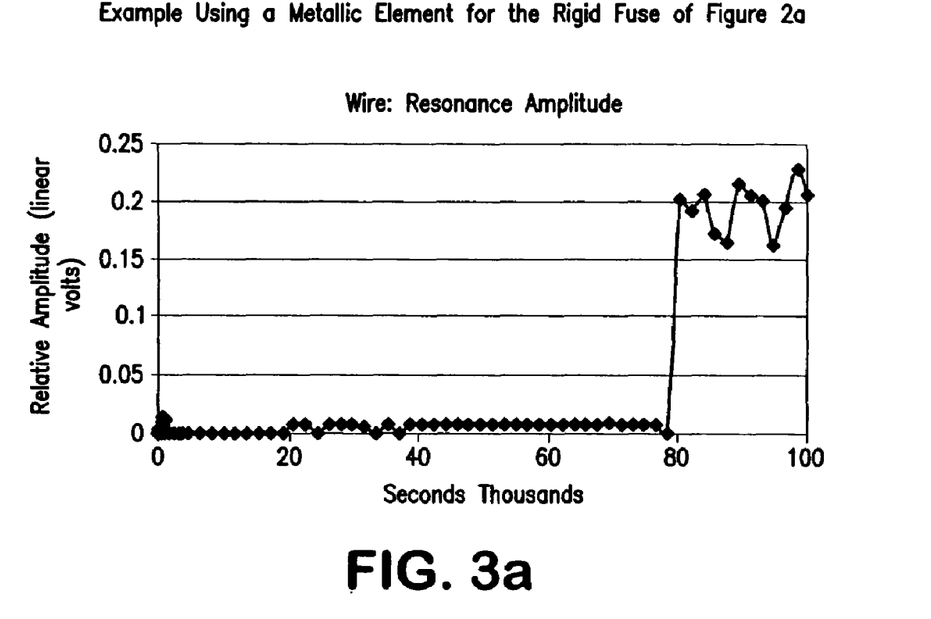

FIG. 3a provides an example where the fusing-element of FIG. 2a consists of a carbon steel wire with a diameter of 0.064 inch. This carbon steel fuse element was welded to the stainless steel tines. The tines and welded ends of the fuse link were coated with a wax to prevent corrosion in a 15% hydrochloric acid solution at ambient temperature. Since the wax is impervious to the hydrochloric acid, only the center of the fusing element will be acid attacked. The tuning fork used for the data collection of FIG. 3a was driven at its resonance frequency by a piezoceramic element. The output of the fork was monitored using the same piezoceramic element in transceive mode. As shown in the figure, there is no significant amplitude until approximately 80,000 seconds of acid exposure have elapsed. Concurrent visual monitoring of the fusing element confirmed that the change in amplitude did correspond to the physical break of the fuse.

A few example applications are provided in the refining process industry. Fluidized catalytic cracking units employ solid catalyst particles to promote the reaction. During upset conditions, these solids may be inadvertently carried over to an improper process stream. This inadvertent carry-over may cause accelerated erosion of the process containment (e.g. the pipe wall). The availability of a corrosion fuse element fabricated from the pressure containment material could provide an early warning of this undesirable condition. Another example from the refinery industry is inadvertent liquid carry-over of sulfuric acid in an alkylation unit.

Another refinery industry example is the application of the fusing element as a detection for an excessive amount of chlorides. In refinery crude distillation units, chlorides enter as part of the crude oil. Although most chlorides or other corrosive species should be removed in advance of the crude unit by the desalter, this removal process is typically incomplete and sometimes inadequate. Chlorides that pass through the crude distillation process may cause acidic corrosion as the service temperature cools and condenses. Although a low level of chlorides may be tolerable to the containment metallurgy, a small concentration increase of chlorides or the net reduction or loss of the chemical neutralization usually employed may cause problematic corrosion. In this case, it may be desirable to fabricate the fusing element from a more corrosion resistant material than the containment material. However, the fusing element is not so robust as to resist corrosion at a desired concentration level. As an example, if the process containment material were carbon steel, the fusing element could be stainless steel. In this case, the fusing element would not corrode under normal operation with a low level of corrosion. However, it would be susceptible to an increase of chloride concentration.

Figure 3B:
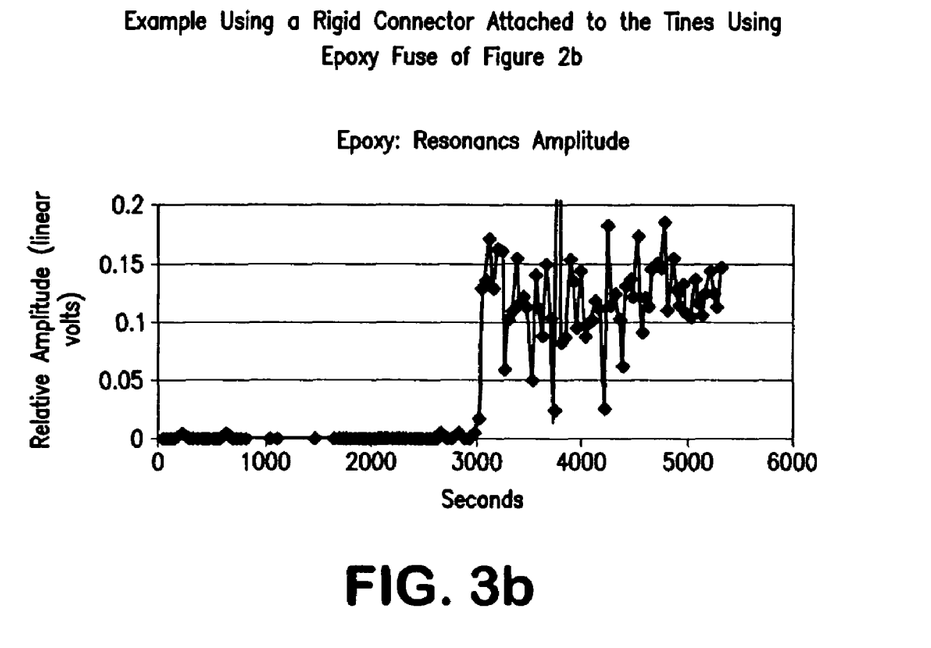
FIG. 3b shows the result using a connector of FIG. 2b. The rigid connector is attached to the tines by epoxy which is the fusing component.

FIG. 3b provides an example using the tuning fork described in FIG. 2b. The example of FIG. 3b uses a rigid connecting element [50] fabricated from a carbon steel wire attached to the tines by epoxy [70]. In this example, the epoxy is the consumable fusing element. The corrosive fluid, a solvent, can attack the epoxy but not the carbon steel wire nor the stainless steel tines. As shown in FIG. 3b, the amplitude of the resonator increases after approximately 3000 seconds of exposure. Visual inspection confirmed that the carbon steel link had separated at the epoxy joint from one of the tines. This separation freed the tines enabling resonance motion as indicated by the amplitude increase.

In an also preferred embodiment, the rigidly connected fuse is installed in a fashion that provides either tension or compression to the fuse element. This tension or compression can be achieved at the time of fabrication by compressing the tines toward each other or tensioning the tines away from each other. In this embodiment, a fuse reaction with the environment that caused a change in mechanical strength would cause the fuse to break. When the element fails due to the change in mechanical properties, the fork resonance would become active and provide an alarm for similar degradation of the equipment being monitored. Examples of such degradation include stress corrosion cracking, high temperature hydrogen attack, and decarburization.

A fusing element that attaches the rigid bar to the tines can be made to be specific for a particular solvent, water, or hydrocarbon material. The fusing element can also be fabricated so that it breaks above a pre-specified concentration. As an example, a polystyrene fusing element could be put into an aqueous stream to detect the presence of an aromatic solvent such as toluene.

Figure 4:
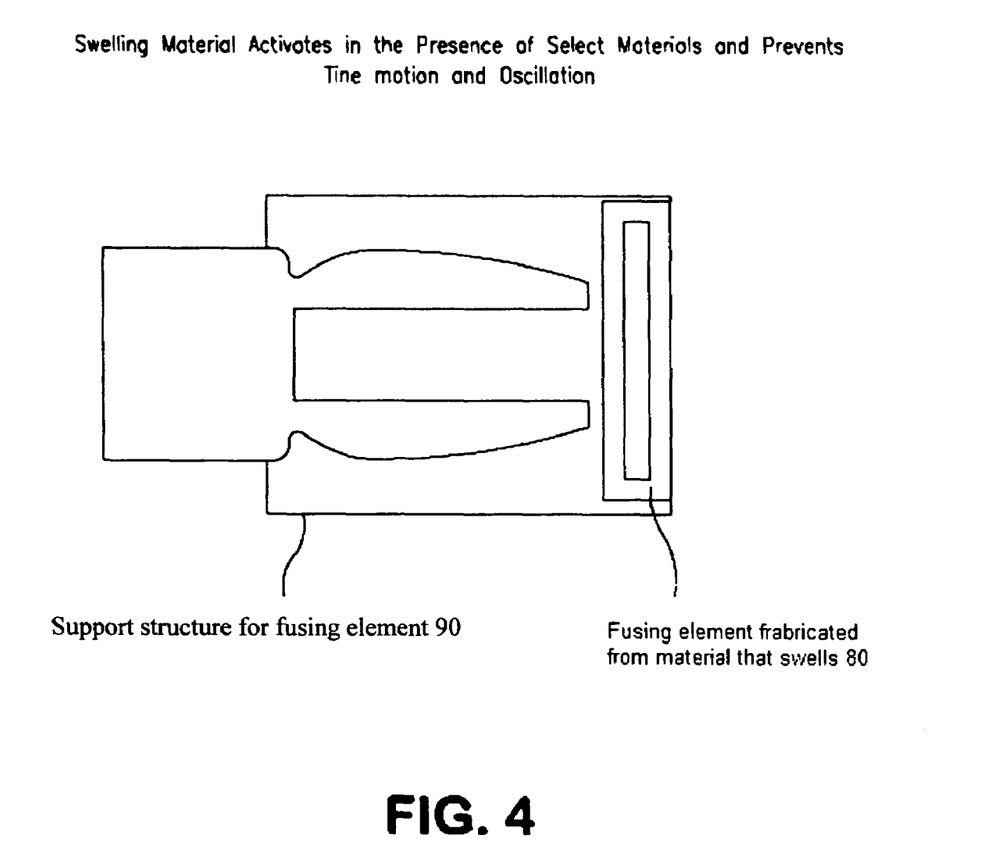
FIG. 4 illustrates an embodiment applying a fusing element that may swell (or shrink) to enable (or disable) the motion of tines. In the unexposed case, the fusing element prevents motion of the tines.

Embodiment where the Fusing Element Employs a Material that May Shrink or Expand In another highly preferred embodiment, a fusing element [80] is employed that may swell (or shrink) to enable (or disable) the motion of tines. The fusing element is positioned by supporting structure [90]. This embodiment, shown in FIG. 4, is particularly attractive for applications where it is desired to detect a low concentration of a contamination fluid in a process stream. The rigid supports [90] are attached to the area supporting the diaphragm. For example, industrial processes often use water as the cooling fluid in a shell and tube heat exchanger. It is often very desirable to quickly detect a breach in the boundary between the cooling water and the process fluid. In this example, the penetration of process fluid to the cooling water causes the process fluid to be the contaminant. By selecting a fusing element that expands when exposed to hydrocarbon will the oscillation to stop when the fusing element touches the tines.

In one configuration, the fusing element does not interfere with the motion of the tines when unexposed to the contaminant. Introduction of the contaminant causes the fusing element to expand (swell), coming in contact with the tines, and preventing motion of the tines. In a separate configuration, the fusing element is in direct contact with the tines preventing their motion when unexposed to the contaminant. Introduction of the contaminant causes the fusing element to shrink, pulling away from the tines and thereby enabling tine motion. The selected configuration will be dependent upon the available materials for shrinking or swelling with the contaminant and service fluids of interest. For example, a silicone-based polymer will have considerable swelling for aviation grade kerosene but very little swelling for a heavier fuel oil.

Embodiment Using a Damping Fuse Element and a Bellows

Figure 5:
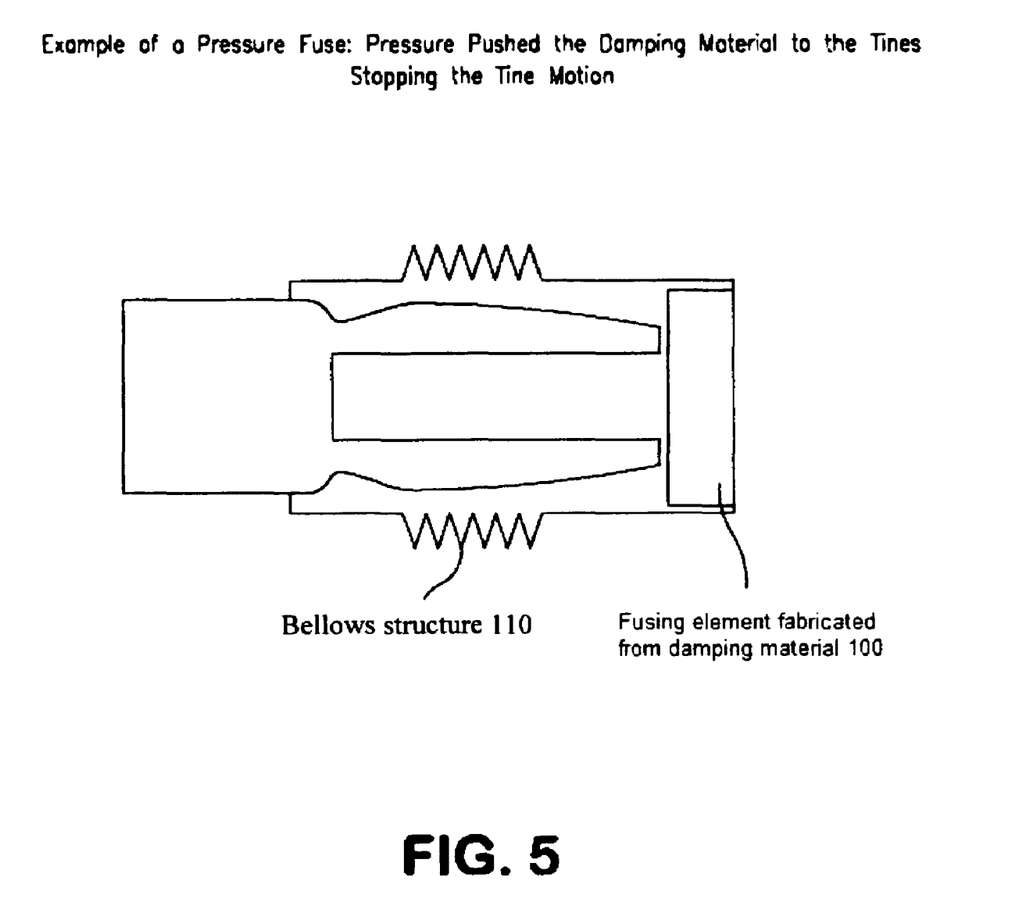
FIG. 5 illustrates an embodiment applying a damping fuse element that is held in contact with (or away from) the tines via a bellows arrangement. Changes in pressure can cause the damping material to move away from (or in contact with) the tines permitting oscillation.

In another preferred embodiment, a fusing element is attached to a bellows. The bellows may compress or expand depending upon the pressure of the process fluid. As depicted in FIG. 5, a damping material [100] is attached to the bellows [110]. Depending upon the pressure, the amount of bellows compression will change. The damping material moves with changes in the amount of bellows compression. When the compression is such that the damping material is in contact with the tines, the tine motion will be disabled. A suitable change in pressure and the bellows compression will move the damping material off of the tines enabling motion. The base case position of the damping material (e.g. the ambient pressure case) may cause the damping material to either be in contact or separate from the tines. The ambient pressure positioning of the damping material will be dependent upon the particular application and will determine whether the device is used to alarm for an over or under pressure condition.

A variant method on the bellows approach is to deploy a bimetallic fixture where the bend is temperature dependent. By suitable selection of the bimetallic materials, this strip can be configured to interfere with the tine motion when a pre-specified temperature limit (high or low) is exceeded.

Embodiment Using a Deposited Fuse Element at the Tip of the Tines

Figure 6:
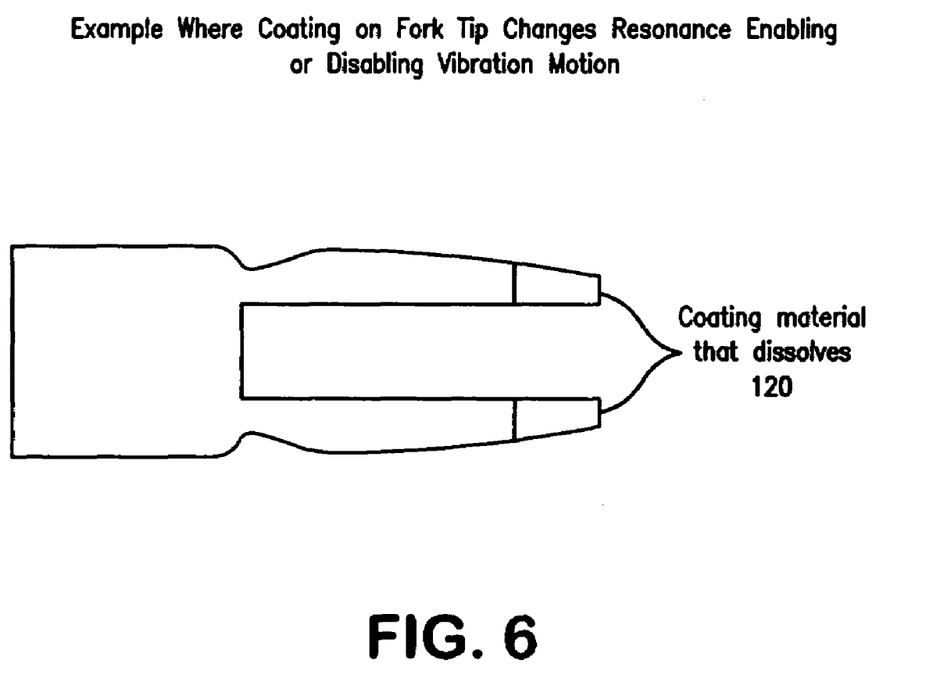
FIG. 6 shows the deposition of the fuse material at the tip of the rod oscillator B.

In another highly preferred embodiment, a fusing element [120] shown in FIG. 6 is applied to the tips of the tines. This fusing element is not compatible with the corrosive or contaminating fluid. The tines are fabricated from a material that is compatible with the service fluid. The mass and thickness of the fusing material is known and/or measured after the deposition. Likewise, the resonance parameters (frequency, amplitude, and Q) are measured before and after the application of the fuse material. The device goes into alarm mode when the resonance parameters change a prescribed amount corresponding to the removal of a substantial amount of the fusing material. The sensitivity or the alarming threshold can be adjusted by the amount of fuse deposition: reducing the amount of deposition increases the threshold sensitivity because there is less material to be removed. An example of this embodiment is the fabrication of a hydrogen fluoride (HF) detector. By using glass as the fuse deposition material, the sensor will alarm when a pre-specified amount of glass is dissolved by the presence of HF. In contrast to thin film glass etching HF sensors which cannot be reused after exposure, the instant invention can be re-armed as long as all of the glass has not been expended. The HF sensor could also be fabricated by a rigid glass fuse as illustrated in FIGS. 3a/b. In this embodiment with a rigid connector, the fuse would need to be replaced before reusing the sensor.

When it is desired for the sensor to alarm from a specified amount of material loss caused by the process fluid, then the fuse deposition material should be selected to reflect this application. In another application, it may be desired for the sensor to alarm in the presence of contamination not normally found in the process stream. In this case, the fuse deposition material must be compatible with the process fluid contaminant.

To prevent premature alarming, electronics can be configured with the tuning fork device of FIG. 6. The electronics can be set to trigger the alarm mode for a pre-specified change in the resonance parameters of amplitude, frequency, and/or Q.

What is claimed is:

1. A sensor to detect the presence of a specified condition in a medium comprising:
   (a) a tuning fork including a diaphragm and tines having an amplitude and a resonance frequency,
   (b) a fuse fixed to said tuning fork wherein the presence of the specified conditions will cause the fuse to change the amplitude of said oscillator tuning fork to or from the amplitude at the resonance frequency wherein said fuse is fixed between said tuning fork tines to prevent motion of the tines.

2. The sensor of claim 1 wherein said condition causes the fuse to change the amplitude at resonance frequency.

3. The sensor of claim 1 wherein said condition causes the fuse to change the amplitude away from the amplitude at or near the resonance frequency.

4. The sensor of claim 1 wherein the specified condition is a corrosive material in said medium.

5. The sensor of claim 4 wherein the specified condition is a corrosive material in said medium causing a change in the mechanical strength of the fuse.

6. The sensor of claim 1 wherein the specified condition is a foreign material in said medium.

7. The sensor of claim 1 wherein the specified condition is an erosive medium.

8. The sensor of claim 1 wherein said tines are under compression.

9. The sensor of claim 1 wherein said tines are under tension.

10. The sensor of claim 1 wherein the specified condition is temperature.

11. A sensor to detect the presence of a specified condition in a medium comprising:
   (a) a tuning fork including a diaphragm and tines having an amplitude and a resonance frequency,
   (b) a fuse fixed to said tuning fork wherein the presence of the specified conditions will cause the fuse to change the amplitude of said oscillator tuning fork to or from the amplitude at the resonance frequency wherein said fuse is fixed to said tuning fork by supports fixed to the diaphragm to prevent motion of the tines.

12. The sensor of claim 11 wherein said supports include expandable members.

13. The sensor of claim 11 wherein the specified condition is pressure.

14. A sensor to detect the presence of a specified condition in a medium comprising:
   (a) a tuning fork including a diaphragm and tines having an amplitude and a resonance frequency,
   (b) a fuse fixed to said tuning fork wherein the presence of the specified conditions will cause the fuse to change the amplitude of said oscillator tuning fork to or from the amplitude at the resonance frequency, wherein said fuse is fixed to said tuning fork by supports fixed to the diaphragm to allow motion of the tines.

15. The sensor claim of claim 14 wherein said supports include contractible members.

16. The sensor of claim 14 wherein the specified condition is pressure.

* * * * *